United States Patent
Holoubek et al.

(10) Patent No.: US 10,779,571 B2
(45) Date of Patent: Sep. 22, 2020

(54) AEROSOL GENERATING DEVICE WITH ANCHORED HEATER

(71) Applicant: Philip Morris Products S.A., Neuchatel (CH)

(72) Inventors: Jiri Holoubek, Roznov p.R. (CZ); Josef Vlk, Chanovice (CZ); Sebastian Schmelzer, Soest (DE)

(73) Assignee: Philip Morris Products S.A., Neuchatel (CH)

( * ) Notice: Subject to any disclaimer, the term of this patent is extended or adjusted under 35 U.S.C. 154(b) by 121 days.

(21) Appl. No.: 15/546,300

(22) PCT Filed: Feb. 1, 2016

(86) PCT No.: PCT/EP2016/052090
§ 371 (c)(1),
(2) Date: Jul. 26, 2017

(87) PCT Pub. No.: WO2016/124552
PCT Pub. Date: Aug. 11, 2016

(65) Prior Publication Data
US 2018/0049471 A1    Feb. 22, 2018

(30) Foreign Application Priority Data
Feb. 5, 2015   (EP) .................................... 15154037

(51) Int. Cl.
*A24F 47/00* (2020.01)
*H01R 13/405* (2006.01)
*A61M 15/06* (2006.01)

(52) U.S. Cl.
CPC ........... *A24F 47/008* (2013.01); *A61M 15/06* (2013.01); *H01R 13/405* (2013.01)

(58) Field of Classification Search
CPC ...... A24F 47/008; H01R 13/41; H01R 13/405
See application file for complete search history.

(56) References Cited

U.S. PATENT DOCUMENTS 4,029,388 A * 6/1977 Knoll ................... H01R 13/405
                                                                439/736
6,206,735 B1 * 3/2001 Zanolli ................ H01R 12/585
                                                                439/404
(Continued)

FOREIGN PATENT DOCUMENTS

CA    2 856 321 A1    5/2013
CN    1906079 A       1/2007
(Continued)

OTHER PUBLICATIONS

International Search Report and Written Opinion dated Apr. 20, 2016 in PCT/EP2016/052090, filed Feb. 1, 2016.
(Continued)

*Primary Examiner* — Alex B Efta
(74) *Attorney, Agent, or Firm* — Oblon, McClelland, Maier & Neustadt, L.L.P.

(57) ABSTRACT

An electrically heated aerosol-generating device is provided, including a heating assembly configured to heat an aerosol-forming substrate to generate an inhalable aerosol, the assembly including a heater and a heater mount, the heater being blade-shaped, including an electrically insulating heater substrate, an electrically resistive heating element supported by the heater substrate, and a through-hole through a thickness of the heater, the heater being insertable into the aerosol-forming substrate and having a length of about 10 mm to about 60 mm, a width of about 2 mm to about 10 mm, and a thickness of about 0.2 mm to about 1 mm, the mount including a moldable material molded around a portion of the heater and extending through the through-hole to couple the heater to the mount so the mount provides structural support to the heater and is configured to allow the heater to be disposed within the device.

10 Claims, 3 Drawing Sheets

(56) References Cited

U.S. PATENT DOCUMENTS

Figure 1:
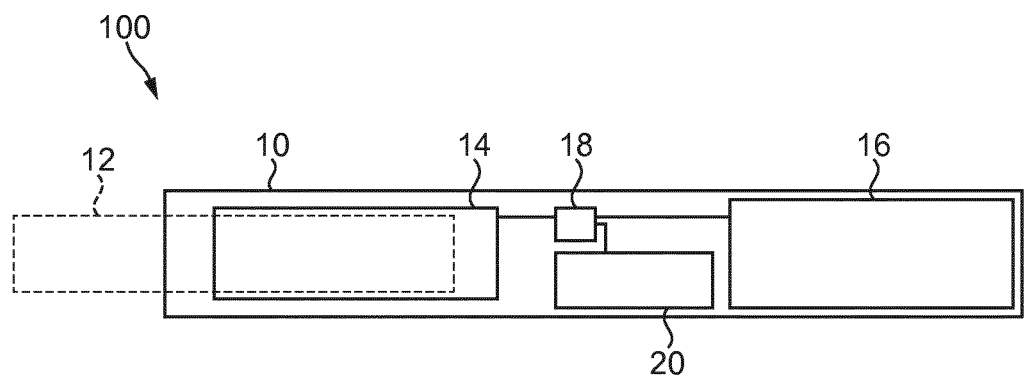

| | | | | |
|---|---|---|---|---|
| 2014/0030932 A1* | 1/2014 | Lee | ................... | H01R 43/24 |
| | | | | 439/693 |
| 2014/0060554 A1 | 3/2014 | Collett et al. | | |
| 2015/0013696 A1 | 1/2015 | Plojoux et al. | | |
| 2015/0027459 A1 | 1/2015 | Collett et al. | | |
| 2015/0163859 A1 | 6/2015 | Schneider et al. | | |

FOREIGN PATENT DOCUMENTS

| | | | |
|---|---|---|---|
| CN | 202052669 U | 11/2011 | |
| CN | 202068930 U | 12/2011 | |
| WO | WO 2011/050964 A1 | 5/2011 | |
| WO | WO 2011/079932 A1 | 7/2011 | |
| WO | WO 2012/085082 A1 | 6/2012 | |
| WO | WO 2013/076098 A2 | 5/2013 | |
| WO | WO 2014/102092 A1 | 7/2014 | |
| WO | WO-2014102092 A1 * | 7/2014 | ........... A24F 47/008 |

OTHER PUBLICATIONS

International Preliminary Report on Patentability and Written Opinion dated Aug. 17, 2017 in PCT/EP2016/052090.
Chinese Office Action dated Apr. 15, 2020, in corresponding Chinese Patent Application No. 201680006460.2, with English Translation, (14 pages).

* cited by examiner

AEROSOL GENERATING DEVICE WITH ANCHORED HEATER

The specification relates to an electrically-heated aerosol-generating device comprising a heating assembly for heating an aerosol-forming substrate to generate an inhalable aerosol. The heating assembly comprises a heater and a heater mount, and the heater is configured to have enhanced anchoring within the heater mount.

There is increasing demand for handheld aerosol-generating devices that are able to deliver aerosol for user inhalation. One particular area of demand is for heated smoking devices in which an aerosol-forming substrate is heated to release volatile flavour compounds, without combustion of the aerosol-forming substrate. The released volatile compounds are conveyed within an aerosol to the user.

Any aerosol-generating device that operates by heating an aerosol-forming substrate must include a heating assembly. A number of different types of heating assembly have been proposed for different types of aerosol-forming substrate.

One type of heating assembly that has been proposed for heated smoking devices operates by inserting a heater into a solid aerosol-forming substrate, such as a plug of tobacco. This arrangement allows the substrate to be heated directly and efficiently. But there are number of technical challenges with this type of heating assembly, including meeting requirements for small size, robustness, low manufacturing cost, sufficient operating temperatures and effective localisation of generated heat.

WO2014/102092 discloses a heating assembly for an aerosol-generating device. The heating assembly includes a heater, having a ceramic substrate and an electrically-resistive track, and a heater mount that is moulded to a holding portion of the heater. The heater is designed to be inserted into, and withdrawn from, a solid aerosol-forming substrate.

During use it has been observed that a tobacco plug (an aerosol-forming substrate) of a smoking article often becomes "stuck" or "adheres" to the heater in the device disclosed in WO2014/102092. Upon pulling the smoking article to remove the article from the device, a force is therefore executed upon the heater. Repeated usage may mean repeated pulling upon the heater due to this adhesion between the heater and the tobacco plug. This may weaken the interface between the heater mount and the heater, thereby loosening the heater. It is important that the heater does not become loosened in its heater mount.

Attempts have been made to increase the "anchorage force" provided by the over-moulded heater mount. One of these attempts involved the addition of a frictional powder the heater in order to increase its anchoring once incorporated into the heater mount. However, this is not a preferred technique, as the heater blades are produced in a clean-room environment, and the use of powders is not welcomed typically in such conditions.

This disclosure provides an electrically-heated aerosol-generating device comprising a heating assembly for heating an aerosol-forming substrate to generate an inhalable aerosol. The heating assembly comprises a heater and a heater mount.

The heater is substantially blade-shaped for insertion into the aerosol-forming substrate and has a length of between 10 mm and 60 mm, a width of between 2 mm and 10 mm, and a thickness of between 0.2 mm and 1 mm. A preferred length may be between 15 mm and 50 mm, for example between 18 mm and 30 mm. A preferred length may be about 19 mm or about 20 mm. A preferred width may be between 3 mm and 7 mm, for example between 4 mm and 6 mm. A preferred width may be about 5 mm. A preferred thickness may be between 0.25 mm and 0.5 mm. A preferred thickness may be about 0.4 mm. The heater comprises an electrically-insulating heater substrate and an electrically-resistive heating element supported by the heater substrate. A through-hole is defined through the thickness of the heater. The heater mount provides structural support to the heater and allows the heater to be located within the aerosol-generating device. The heater mount is formed from a mouldable material that is moulded around a portion of the heater and extends through the though-hole to couple to the heater to the heater mount. The heater may have a tapered or pointed end to facilitate insertion into an aerosol-forming substrate.

The heater mount is preferably moulded to a portion of the heater that does not significantly increase in temperature during operation. Such a portion may be termed a holding portion and the heating element may have lower resistivity at this portion so that it does not heat up to a significant degree on the passage of an operational current. The through-hole is located in the holding portion.

Without a through-hole, the heater is anchored to the heater mount by the interface formed between the heater and the over-moulded mount. Repeated use of the device weakens this interface leading to the loosening of the heater. The presence of the through-hole allows the formation of a mechanical tie. The mouldable material flows through the through-hole and joins. The link or tie thus formed resists movement of the heater even if the interface between the mouldable material and the heater breaks down. Furthermore, the increased anchoring effect provided by the mouldable material flowing through the through-hole prevents excessive movement of the heater within the heater mount, which helps prevent breakdown of the interface between the heater and the heater mount.

Preferably the hole is dimensioned to have a maximum diameter of between 0.8 mm and 3 mm, for example between 1 mm and 2.5 mm, for example about 2 mm. The hole may not be circular. The term diameter is used to indicate the maximum dimension across the mouth of the hole. The holes could, for example, be square holes and the maximum diameter may be the dimension extending from one corner of the square to its diagonally opposed corner.

There may be two or more through-holes defined through the thickness of the heater. In this case the mouldable material of the heater mount extends through each of the two or more through-holes. For example the holding portion of the heater may have two through-holes, or three through-holes, or four through-holes. The holes may be arranged in specific patterns to provide optimum anchoring effects.

The heater may further comprise one or more outwardly-extending lugs to enhance coupling of the heater mount to the heater. The heater is substantially blade-shaped and therefore has two substantially parallel edges and two substantially parallel faces. Lugs may extend or project outwardly from the faces or the edges and may provide further mechanical anchoring of the heater.

Alternatively, or in addition, the heater may further comprise one or more inwardly-extending notches or grooves to enhance coupling of the heater mount to the heater.

Advantageously, the mouldable material of the heater mount may be a polymeric material, for example polyether ether ketone (PEEK). The heater substrate may be formed from a ceramic material, for example zirconia or alumina.

The through-hole may be formed in the heater before or after the electrically-resistive heating element is formed on the heater substrate. A device may be formed by fixing or coupling a heating assembly to, or within, a housing.

One method of manufacturing an aerosol-generating device may comprise the steps of: providing a heater substrate having a length of between 10 mm and 60 mm, a width of between 2 mm and 10 mm, and a thickness of between 0.2 mm and 1 mm, the heater substrate being formed from an electrically-insulating material and having a through-hole defined through its thickness; depositing one or more electrically-resistive heating elements on the heater substrate to form a heater; coupling a heater mount to the heater to form a heater assembly, the heater mount being formed from a mouldable material that is moulded around a portion of the heater such that the mouldable material extends through the through-hole, and locating the heater assembly in a housing.

If the heater substrate is a ceramic the through-hole may be formed before the ceramic has been fired. The through-hole may be formed by machining after firing, for example by laser machining or by drilling. The housing may comprise a power source and the method may include steps of connecting the electrically-resisting heating element to the power source.

One method of manufacturing an aerosol-generating device comprising the steps of: providing a heater substrate having a length of between 10 mm and 60 mm, a width of between 2 mm and 10 mm, and a thickness of between 0.2 mm and 1 mm, the heater substrate being formed from an electrically-insulating; depositing one or more electrically-resistive heating elements on the heater substrate to form a heater, forming a through-hole through the thickness of the heater; coupling a heater mount to the heater to form a heater assembly, the heater mount being formed from a mouldable material that is moulded around a portion of the heater such that the mouldable material extends through the through-hole, and locating the heater assembly in a housing.

The through-hole may be formed by machining, for example by laser machining or by drilling. The housing may comprise a power source and the method may include steps of connecting the electrically-resisting heating element to the power source.

As used herein, the term 'electrically-heated aerosol-generating device' is used to describe a device that interacts with an aerosol-forming substrate of an aerosol-generating article to generate an aerosol. Preferably, the aerosol-generating device is a smoking device that interacts with an aerosol-forming substrate of a heated aerosol-generating article to generate an aerosol that is directly inhalable into a user's lungs thorough the user's mouth. Preferably, the aerosol-generating device interacts with an aerosol-generating article to allow air to flow through the aerosol-forming substrate.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. A smoking article comprising an aerosol-forming substrate comprising tobacco is referred to as a tobacco stick.

The heater mount provides structural support to the heater and allows it to be securely fixed within an aerosol-generating device. The use of a mouldable material such as a mouldable polymer allows the heater mount to be moulded around the heater and thereby firmly hold the heater. It also allows the heater mount to be produced with a desired external shape and dimensions in an inexpensive manner.

The use of a polymer to hold the heater means that the temperature of the heater in the vicinity of the heater mount should be controlled to be below the temperature at which the polymer will melt burn or otherwise degrade. At the same time the temperature of the portion of the heater inserted within the aerosol-forming substrate must be sufficient, during use, to produce an aerosol with the desired properties. It is therefore desirable to ensure that a holding portion of the heating element, that is at least at those points of the heater in contact with the heater mount, remain below a maximum allowable temperature during use.

In an electrically resistive heater, the heat produced by the heater is dependent on the resistance of the heating element. For a given current, the higher the resistance of the heating element the more heat is produced. It is desirable that most of the heat produced is produced by a part of the heating element that is inserted into an aerosol-forming substrate, that is the part of the heating element supported by an insertion portion or heating portion of the heater. Accordingly it may be desirable that the insertion portion of the heater supports a part of the heating element having a greater electrical resistance per unit length than the part of the heating element supported by the holding portion of the heater.

Advantageously, the heating element may be formed from different materials. A first part, or heating part, of the heating element (i.e. that portion supported by the insertion or heating portion of the heater) may be formed from a first material and a holding part of the heating element (i.e. that part supported by a holding portion of the heater) may be formed from a second material, wherein the first material has a greater electrical resistivity coefficient than the second material. For example, the first material may be Ni—Cr (Nickel-Chromium), platinum, tungsten or alloy wire and the second material may be gold or silver or copper. The dimensions of the first and second parts of the heating element may also differ to provide for a lower electrical resistance per unit length in the second portion.

The heater substrate is formed from an electrically insulating material and may be a ceramic material such as Zirconia or Alumina. The heater substrate may provide a mechanically stable support for the heating element over a wide range of temperatures and may provide a rigid structure suitable for insertion into an aerosol-forming substrate. The heater substrate comprises a planar surface on which the heating element is positioned and may comprise a tapered end configured to allow for insertion into an aerosol-forming substrate. The heater substrate advantageously has a thermal conductivity of less than or equal to 2 Watts per metre Kelvin.

Heaters having different configurations of heater element materials and heater substrate materials are set out in WO2014/102092.

The aerosol-generating device preferably comprises a housing defining a cavity surrounding an insertion portion of the heater. The cavity is configured to receive an aerosol-forming article containing an aerosol forming substrate. The heater mount may form a surface closing one end of the cavity.

The device is preferably a portable or handheld device that is comfortable to hold between the fingers of a single hand. The device may be substantially cylindrical in shape and has a length of between 70 and 120 mm. The maximum diameter of the device is preferably between 10 and 20 mm. In one embodiment the device has a polygonal cross section and has a protruding button formed on one face. In this embodiment, the diameter of the device is between 12.7 and 13.65 mm taken from a flat face to an opposing flat face; between 13.4 and 14.2 taken from an edge to an opposing edge (i.e., from the intersection of two faces on one side of the device to a corresponding intersection on the other side), and between 14.2 and 15 mm taken from a top of the button to an opposing bottom flat face.

The device may include other heaters in addition to the heater assembly according to the first aspect. For example the device may include an external heater positioned around a perimeter of the cavity. An external heater may take any suitable form. For example, an external heater may take the form of one or more flexible heating foils on a dielectric substrate, such as polyimide. The flexible heating foils can be shaped to conform to the perimeter of the cavity. Alternatively, an external heater may take the form of a metallic grid or grids, a flexible printed circuit board, a moulded interconnect device (MID), ceramic heater, flexible carbon fibre heater or may be formed using a coating technique, such as plasma vapour deposition, on a suitable shaped substrate. An external heater may also be formed using a metal having a defined relationship between temperature and resistivity. In such an exemplary device, the metal may be formed as a track between two layers of suitable insulating materials. An external heater formed in this manner may be used to both heat and monitor the temperature of the external heater during operation.

The power supply of the device may be any suitable power supply, for example a DC voltage source such as a battery. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The device preferably comprises a control element. The control element may be a simple switch. Alternatively the control element may be electric circuitry and may comprise one or more microprocessors or microcontrollers.

The disclosure provides an aerosol-generating system comprising an aerosol-generating device as described above and one or more aerosol-forming articles configured to be received in a cavity of the aerosol-generating device.

The aerosol-forming article may be a smoking article. During operation a smoking article containing the aerosol-forming substrate may be partially contained within the aerosol-generating device.

The smoking article may be substantially cylindrical in shape. The smoking article may be substantially elongate. The smoking article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length.

The smoking article may have a total length between approximately 30 mm and approximately 100 mm. The smoking article may have an external diameter between approximately 5 mm and approximately 12 mm. The smoking article may comprise a filter plug. The filter plug may be located at a downstream end of the smoking article. The filter plug may be a cellulose acetate filter plug. The filter plug is approximately 7 mm in length in one embodiment, but may have a length of between approximately 5 mm to approximately 10 mm.

In one embodiment, the smoking article has a total length of approximately 45 mm. The smoking article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The smoking article may comprise an outer paper wrapper. Further, the smoking article may comprise a separation between the aerosol-forming substrate and the filter plug. The separation may be approximately 18 mm, but may be in the range of approximately 5 mm to approximately 25 mm.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former that facilitates the formation of a dense and stable aerosol. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise combining one or both of tobacco leaf lamina and tobacco leaf stems. Alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

In a particularly preferred embodiment, the aerosol-forming substrate comprises a gathered crimpled sheet of homogenised tobacco material. As used herein, the term 'crimped sheet' denotes a sheet having a plurality of substantially parallel ridges or corrugations. Preferably, when the aerosol-generating article has been assembled, the substantially parallel ridges or corrugations extend along or parallel to the longitudinal axis of the aerosol-generating article. This advantageously facilitates gathering of the crimped sheet of homogenised tobacco material to form the aerosol-forming substrate. However, it will be appreciated that crimped sheets of homogenised tobacco material for inclusion in the aerosol-generating article may alternatively or in addition have a plurality of substantially parallel ridges or corrugations that are disposed at an acute or obtuse angle to the longitudinal axis of the aerosol-generating article when the aerosol-generating article has been assembled. In certain embodiments, the aerosol-forming substrate may comprise a gathered sheet of homogenised tobacco material that is substantially evenly textured over substantially its entire surface. For example, the aerosol-forming substrate may comprise a gathered crimped sheet of homogenised tobacco material comprising a plurality of substantially parallel ridges or corrugations that are substantially evenly spaced-apart across the width of the sheet.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

The aerosol-generating system is a combination of an aerosol-generating device and one or more aerosol-generating articles for use with the device. However, aerosol-generating system may include additional components, such as for example a charging unit for recharging an on-board electric power supply in an electrically operated or electric aerosol-generating device Although the disclosure has been described by reference to different aspects, it should be clear that features described in relation to one aspect of the disclosure may be applied to the other aspects of the disclosure.

Embodiments of the invention will now be described in detail, by way of example only, with reference to the accompanying drawings, in which:

FIG. 1 is a schematic diagram of an aerosol generating device;

FIG. 2 is a schematic cross-section of a front end of an aerosol-generating device of the type shown in FIG. 1, with the heater inserted into a smoking article;

FIG. 3 is a schematic illustration of a heating assembly in accordance with the present invention;

FIG. 4 is a cross-section of a portion of the heating assembly of FIG. 3

FIG. 5 is a schematic illustration of an alternative heating assembly in accordance with the present invention;

FIG. 6 is a schematic illustration of an alternative heating assembly in accordance with the present invention.

In FIG. 1, the components of an embodiment of an electrically heated aerosol-generating system 100 are shown in a simplified manner. Particularly, the elements of the electrically heated aerosol-generating system 100 are not drawn to scale in FIG. 1. Elements that are not relevant for the understanding of this embodiment have been omitted to simplify FIG. 1.

The electrically heated aerosol generating system 100 comprises an aerosol-generating device having a housing 10, and an aerosol-forming article 12, for example a tobacco stick. The aerosol-forming article 12 includes an aerosol-forming substrate that is pushed inside the housing 10 to come into thermal proximity with a portion of a heater 14. The aerosol-forming substrate will release a range of volatile compounds at different temperatures.

Within the housing 10 there is an electrical energy supply 16, for example a rechargeable lithium ion battery. A controller 18 is connected to the heater 14, the electrical energy supply 16, and a user interface 20, for example a button or display. The controller 18 controls the power supplied to the heater 14 in order to regulate its temperature. Typically the aerosol-forming substrate is heated to a temperature of between 250 and 450 degrees centigrade.

FIG. 2 is a schematic cross-section of a front end of an aerosol-generating device of the type shown in FIG. 1, with the heater 14 inserted into the aerosol-forming article 12, which in this embodiment is a smoking article. The aerosol-generating device is illustrated in engagement with the aerosol-generating article 12 for consumption of the aerosol-generating article 12 by a user.

The housing 10 of aerosol-generating device defines a cavity, open at the proximal end (or mouth end), for receiving an aerosol-generating article 12 for consumption. The distal end of the cavity is spanned by a heating assembly 24 comprising a heater 14 and a heater mount 26. The heater 14 is retained by the heater mount 26 such that an active heating area (heating portion) of the heater is located within the cavity. The active heating area of the heater 14 is positioned within a distal end of the aerosol-generating article 12 when the aerosol-generating article 12 is fully received within the cavity. The heater mount is formed from polyether ether ketone and is moulded around a holding portion of the heater. A first end of the heater, including the heating portion, extends from one side of the heater mount. A second end of the heater, including a connection portion, extends from the other side of the heater mount.

The heater 14 is shaped in the form of a blade terminating in a point. That is, the heater has a length dimension that is greater than its width dimension, which is greater than its thickness dimension. First and second faces of the heater are defined by the width and length of the heater.

An exemplary aerosol-forming article, as illustrated in FIG. 2, can be described as follows. The aerosol-generating article 12 comprises four elements: an aerosol-forming substrate 30, a support element, such as a hollow tube 40, a transfer section 50, and a mouthpiece filter 60. These four elements are arranged sequentially and in coaxial alignment and are assembled by a cigarette paper 70 to form a rod. When assembled, the aerosol-forming article is 45 millimetres long and has a diameter of 7 millimetres.

The aerosol-forming substrate comprises a bundle of crimped cast-leaf tobacco wrapped in a filter paper (not shown) to form a plug. The cast-leaf tobacco includes one or more aerosol formers, such as glycerine.

The hollow tube 40 is located immediately adjacent the aerosol-forming substrate 30 and is formed from a tube of cellulose acetate. The tube 40 defines an aperture having a diameter of 3 millimetres. One function of the hollow tube 40 is to locate the aerosol-forming substrate 30 towards the distal end 23 of the rod 21 so that it can be contacted with the heater. The hollow tube 40 acts to prevent the aerosol-generating substrate 30 from being forced along the rod towards the mouthpiece when a heater is inserted into the aerosol-forming substrate 30.

The transfer section 50 comprises a thin-walled tube of 18 millimetres in length. The transfer section 50 allows volatile substances released from the aerosol-forming substrate 30 to pass along the article towards the mouthpiece filter 60. The volatile substances may cool within the transfer section to form an aerosol.

The mouthpiece filter 60 is a conventional mouthpiece filter formed from cellulose acetate, and having a length of approximately 7.5 millimetres.

The four elements identified above are assembled by being tightly wrapped within a cigarette paper 70. The paper in this specific embodiment is a standard cigarette paper having standard properties or classification. The paper in this specific embodiment is a conventional cigarette paper. The interface between the paper and each of the elements locates the elements and defines the aerosol-forming article 12.

As the aerosol-generating article 12 is pushed into the cavity, the tapered point of the heater engages with the aerosol-forming substrate 30. By applying a force to the aerosol-forming article, the heater penetrates into the aerosol-forming substrate 30. When the aerosol-forming article 12 is properly engaged with the aerosol-generating device, the heater 14 is inserted into the aerosol-forming substrate 30. When the heater is actuated, the aerosol-forming substrate 30 is warmed and volatile substances are generated or evolved. As a user draws on the mouthpiece filter 60, air is drawn into the aerosol-forming article and the volatile substances condense to form an inhalable aerosol. This aerosol passes through the mouthpiece filter 60 of the aerosol-forming article and into the user's mouth.

Figure 2:
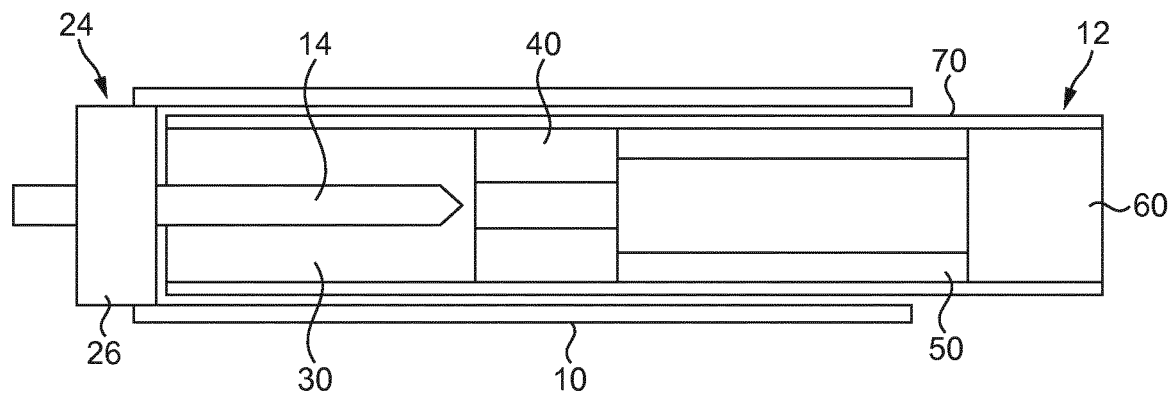
Figure 3:
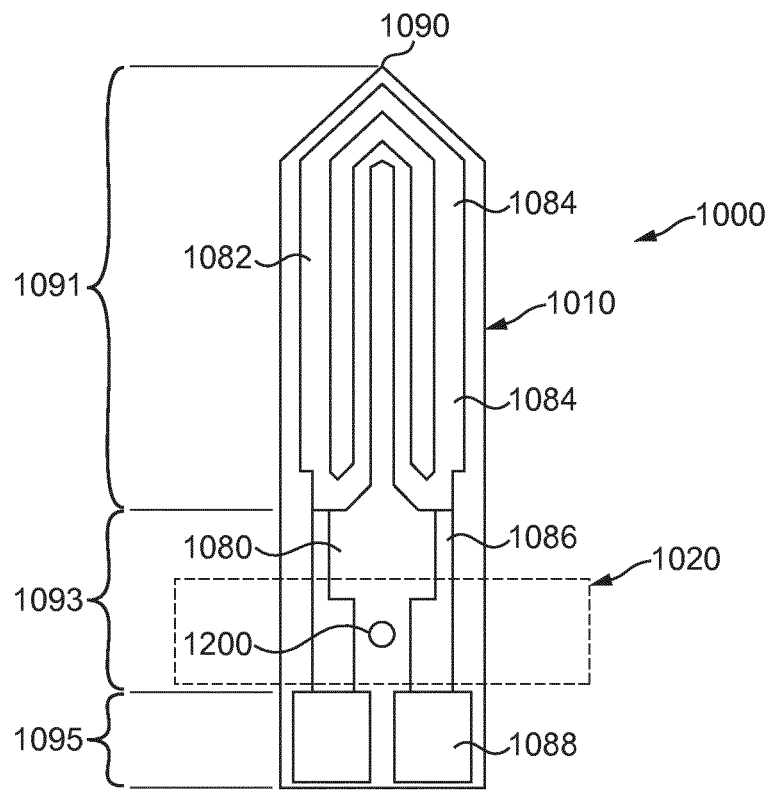

FIG. 3 illustrates a heating assembly 1000 of the type mounted in the device shown in FIG. 2 in greater detail. The heating assembly comprises a heater 1010 and a heater mount 1020. The heater mount is moulded around the heater at a holding portion of the heater. The heater mount is illustrated with dotted lines so that the entire heater is visible. The heater 1010 comprises an electrically insulating heater substrate 1080, which defines the shape of the heater 1010. The heater substrate 1080 is formed from an electrically insulating material, which may be, for example, alumina (Al$_2$O$_3$) or stabilized zirconia (ZrO$_2$). It will be apparent to one of ordinary skill in the art that the electrically insulating material may be any suitable electrically insulating material and that many ceramic materials are suitable for use as the electrically insulating substrate. The heater substrate 1080 is substantially blade-shaped. That is, the heater substrate has a length that in use extends along the longitudinal axis of an aerosol-forming article engaged with the heater, a width and a thickness. The width is greater than the thickness. In a specific embodiment the heater substrate has a length of 19.2 mm, a width of 4.9 mm and a thickness of 0.38 mm. The heater substrate 1080 terminates in a point or spike 1090 for penetrating an aerosol-forming substrate 30.

A heating element 1082 formed from electrically conductive material is deposited on a planar surface of the heater substrate 1080 using evaporation or any other suitable technique. The heating element is formed having three distinct parts. A first part 1084 is formed from platinum. The first part is positioned in the heating portion 1091 of the heater. This is the area of the heater which reaches the maximum temperature and provides heat to an aerosol-forming substrate in use. The first part 1084 of the heating element is substantially U-shaped or in the shape of a hairpin. A second part 1086 is formed from gold. The second part comprises two parallel tracks, each connected to an end of the first part 1084. The second part 1086 spans the holding portion 1093 of the heater, which is the area of the heater that is in contact with the heater mount 1020. A third part 1088 is formed from silver. The third part is positioned in the connecting portion 1095 and provides bonding pads to which external wires can be fixed using solder paste or other bonding techniques. The third part comprises two parallel pads, each connected to an end of one of the parallel tracks of the second part 1086, opposite to the first part 1084. The third part 1088 is positioned on an opposite side of the heater mount to the first part.

The shape, thickness and width of the first, second and third parts may be chosen to provide the desired resistance and temperature distribution in use. However, the first part has a significantly greater electrical resistance per unit length than the second and third parts and, as a result, when an electrical current passes through the heating element 1082, it is the first part that generates the most heat and so reaches the highest temperature. The second and third parts are configured to have a very low electrical resistance and so provide very little Joule heating. The total electrical resistance of the heating element is about 0.80 Ohms at 0° C., rising to about 2 Ohms when the active heating portion 1091 reaches 400° C. The battery voltage of the lithium ion battery is around 3.7 Volts so that the typical peak current supplied by the power supply (at 0° C.) is around 4.6 A.

Platinum has a positive temperature coefficient of resistance and so the electrical resistance of the first part 1084 increases with increasing temperature. Gold and silver have lower temperature coefficients of resistance, and the second and third parts will not experience as great a temperature rise as the first part.

A through-hole 1200 is defined through the thickness of the heater substrate between the parallel conductive tracks in the holding portion of the heater.

Figure 4:
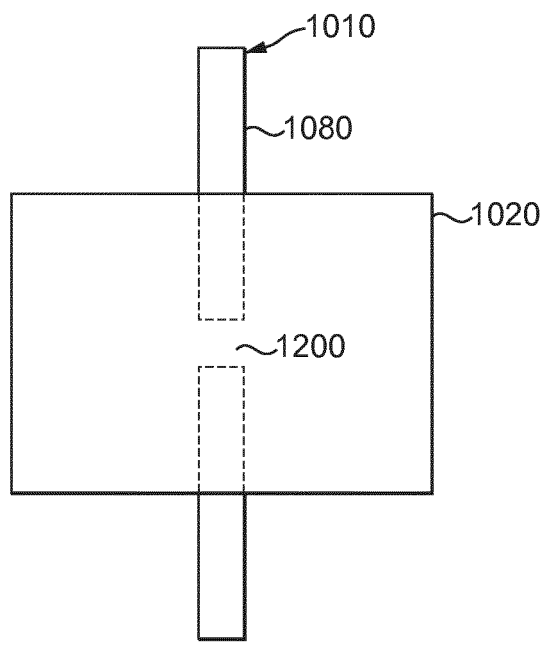

The heater mount 1020 is formed from polyether ether ketone (PEEK) and is injection moulded around the heater at the holding portion 1093. As can be seen in FIG. 4, the PEEK flows through the through-hole 1200, thereby locking the heater to the heater mount.

In this embodiment the heater mount 1020 has a circular cross-section to engage a circular housing 10 of the aerosol-generating device. However, the heater mount may be moulded to have any desired shape and any desired engagement features for engaging with other components of the aerosol-generating device.

A heater assembly as illustrated in FIG. 3 may be mounted in a housing of an aerosol-generating device with the contacts coupled to a power supply. The heater can then be inserted into an aerosol-forming substrate, which is heated when the heater is actuated.

Figure 5:
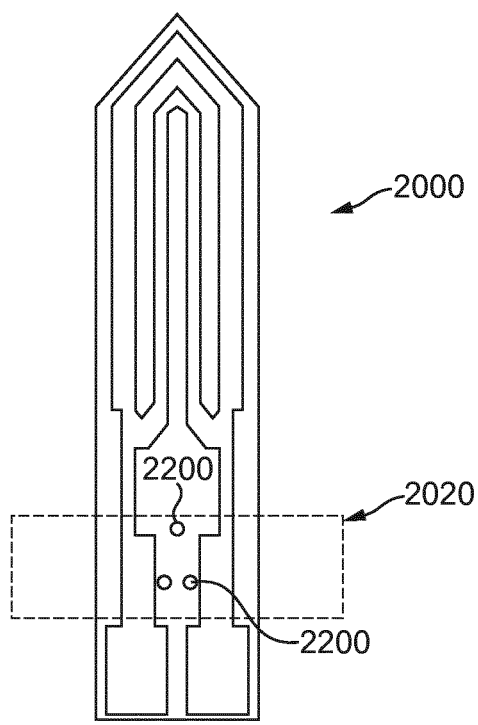

FIG. 5 illustrates an alternative embodiment of a heating assembly. The heating assembly 2000 is as described above in relation to FIG. 3, with the difference that three through-holes 2200 are defined through the thickness of the heater in the holding portion. As before, the material of the heater mount 2020 flows through the through-holes to mechanically lock the heater mount to the heater. The use of three through-holes may increase the anchoring effect compared to a single through-hole.

Figure 6:
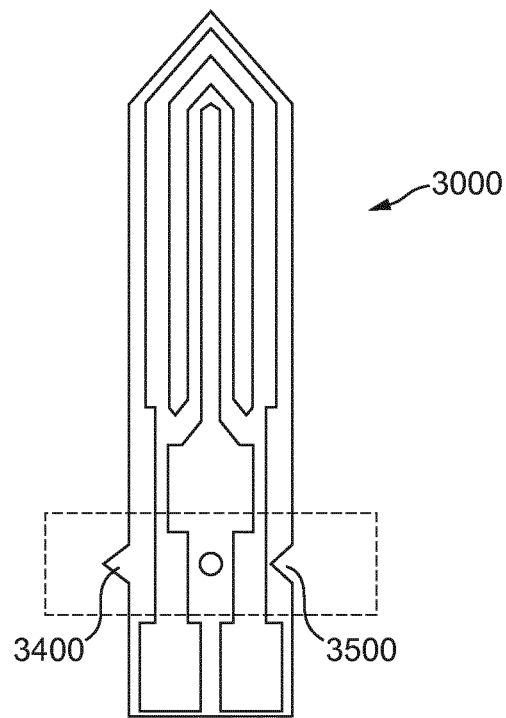

FIG. 6 illustrates an alternative embodiment of a heating assembly. The heating assembly 3000 is as described above in relation to FIG. 3, with the difference that an outwardly extending lug 3400, and an inwardly-extending notch 3500 are defined in the heater in the holding portion. The use of notches and lugs may increase the anchoring effect compared to use of only the through-hole The exemplary embodiments described above illustrate but are not limiting. In view of the above discussed exemplary embodiments, other embodiments consistent with the above exemplary embodiments will now be apparent to one of ordinary skill in the art.

The invention claimed is:

1. An electrically heated aerosol-generating device, comprising:

a heating assembly configured to heat an aerosol-forming substrate to generate an inhalable aerosol, the heating assembly comprising a heater and a heater mount, the heater being substantially blade-shaped and comprising an electrically insulating heater substrate, an electrically resistive heating element supported by the electrically insulating heater substrate, a through-hole defined through a thickness of the heater, and an outwardly extending lug and an inwardly extending notch disposed at opposite sides of the heater along a plane that passes through the heater and the through-hole in a direction substantially perpendicular to a longitudinal axis of the heater, the through-hole being between the lug and the notch along the plane and extending through the thickness of the heater in a direction that is substantially perpendicular to a direction of extension of the lug and the notch, wherein the heater is configured to be inserted into the aerosol-forming substrate and has a length of between about 10 mm and about 60 mm, a width of between about 2 mm and about 10 mm, and a thickness of between about 0.2 mm and about 1 mm, and the heater mount is formed from a moldable material molded around a portion of the heater and extending through the through-hole to couple the heater to the heater mount, wherein the heater mount provides structural support to the heater and is configured to allow the heater to be disposed within the aerosol-generating device.

2. The electrically heated aerosol-generating device according to claim 1, wherein the through-hole has a maximum diameter of between about 1 mm and about 3 mm.

3. The electrically heated aerosol-generating device according to claim 1, wherein the through-hole has a maximum diameter of about 2.5 mm.

4. The electrically heated aerosol-generating device according to claim 1, wherein at least two through-holes are defined through the thickness of the heater, the moldable material of the heater mount extending through each of the at least two through-holes.

5. The electrically heated aerosol-generating device according to claim 1, wherein the outwardly extending lug is configured to enhance coupling of the heater mount to the heater.

6. The electrically heated aerosol-generating device according to claim 1, wherein the inwardly extending notch is configured to enhance coupling of the heater mount to the heater.

7. The electrically heated aerosol-generating device according to claim 1, wherein the moldable material of the heater mount is a polymeric material.

8. The electrically heated aerosol-generating device according to claim 1, wherein the moldable material of the heater mount is polyether ether ketone (PEEK).

9. The electrically heated aerosol-generating device according to claim 1, wherein the electrically insulating heater substrate is formed from a ceramic material.

10. The electrically heated aerosol-generating device according to claim 1, wherein the electrically insulating heater substrate is formed from zirconia or alumina.

* * * * *